(12) United States Patent
Buehring et al.

(10) Patent No.: US 9,052,316 B2
(45) Date of Patent: Jun. 9, 2015

(54) ISOLATION AND/OR IDENTIFICATION OF STEM CELLS HAVING ADIPOCYTIC, CHONDROCYTIC AND PANCREATIC DIFFERENTIATION POTENTIAL

(75) Inventors: Hans-Joerg Buehring, Tubingen (DE); Sabrina Treml, Rottenburg (DE); Reiner Lammers, Tubingen (DE)

(73) Assignee: EBERHARD-KARLS-UNIVERSITAET TUEBINGEN UNIVERSITAETSKLINIKUM, Tuebingen (DE)

( * ) Notice: Subject to any disclaimer, the term of this patent is extended or adjusted under 35 U.S.C. 154(b) by 680 days.

(21) Appl. No.: 12/980,092

(22) Filed: Dec. 28, 2010

(65) Prior Publication Data

US 2011/0117575 A1    May 19, 2011

Related U.S. Application Data

(63) Continuation of application No. PCT/EP2009/004614, filed on Jun. 26, 2009.

(30) Foreign Application Priority Data

Jun. 30, 2008 (DE) .......................... 10 2008 032 236

(51) Int. Cl.
*G01N 33/531* (2006.01)
*G01N 33/569* (2006.01)
*C07K 16/28* (2006.01)
(Continued)

(52) U.S. Cl.
CPC ........ *G01N 33/56966* (2013.01); *G01N 33/531* (2013.01); *C07K 16/2803* (2013.01); *C07K 16/40* (2013.01); *C12N 5/0663* (2013.01)

(58) Field of Classification Search
USPC ................... 435/7.1, 7.2, 325, 372, 374, 377; 436/63, 64; 530/387.1, 388.1, 396
See application file for complete search history.

(56) References Cited

U.S. PATENT DOCUMENTS

7,364,863 B2 * 4/2008 Buhring et al. ................ 435/7.1
8,163,495 B2 * 4/2012 Buhring et al. ................ 435/7.1
(Continued)

FOREIGN PATENT DOCUMENTS

DE    102006043625       3/2008
EP         1901063   *   3/2008   ............. G01N 33/50
(Continued)

OTHER PUBLICATIONS

Ding et al. TNF-α and IL-1β inhibit RUNX2 and collagen expression but increase alkaline phosphatase activity and mineralization in human mesenchymal stem cells, Life Sciences 84: 499-504 (Apr. 10, 2009).*
(Continued)

*Primary Examiner* — Gail R Gabel
(74) *Attorney, Agent, or Firm* — Casimir Jones S.C.

(57) ABSTRACT

The present invention relates to a method for isolating and/or identifying stem cells having adipocytic, chondrocytic and pancreatic differentiation potential, wherein an antibody is used that binds to the antigen TNAP, alone or in combination with an antibody that binds to the cell surface antigen CD56. The invention also relates to stem cells isolated by the method according to the invention for treating defects or damages or diseases in bone or cartilage of a patient in need thereof.

11 Claims, 8 Drawing Sheets

(51) Int. Cl.
    *C07K 16/40*     (2006.01)
    *C12N 5/0775*    (2010.01)

(56) References Cited

U.S. PATENT DOCUMENTS

| | | | |
|---|---|---|---|
| 8,367,405 B2 * | 2/2013 | Gronthos et al. | 435/325 |
| 2011/0117575 A1 | 5/2011 | Buehring et al. | |

FOREIGN PATENT DOCUMENTS

| | | |
|---|---|---|
| WO | 2004/025293 | 3/2004 |
| WO | 2006/108229 | 10/2006 |

OTHER PUBLICATIONS

Battula et al. Isolation of functionally distinct mesenchymal stem cell subsets using antibodies against CD56, CD271, and mesenchymal stem cell antigen-1, Haematologica 94 (2): 173-184 (Feb. 3, 2009).*

Buehring et al. Novel Markers for the Prospective Isolation of Human MSC, Annals of the New York Academy of Sciences, New York Academy of Sciences, New York, NY, US (Sep. 16, 2006).*

Koehler, et al., "Continuous cultures of fused cells secreting antibody of predefined specificity," Nature (1975), 256:495-497.

Sharon, et al., "Expression of a VHCα Chimaeric Protein in Mouse Myeloma Cells," Nature (1984), 309:364-367.

Kibbe, A., "Handbook of Pharmaceutical Excipients," 3rd Ed. (2000), American Pharmaceutical Association of Pharmaceutical Press, Table of Contents.

Buehring Hans-Joerg et al., "Novel Markers for the Prospective Isolation of Human MSC", Annals of the New York Academy of Sciences, New York Academy of Sciences, New York, NY, US, Sep. 16, 2006.

Vogel Wichard et al, "Heterogeneity Among Human Bone Marrow-Derived Mesenchymal Stem Cells land Neural Progenitor Cells," Haematologica, Fondazione Ferrata Storti, Rom, Italy, vol. 88, No. 2, Feb. 1, 2003, pp. 126-133.

Buhring, Hans-Jorg, et al., "Novel Markers for the Prospective Isolation of Human MSC," 2007, Ann. N.Y. Sci., vol. 1106 (2007)), pp. 262-271.

Battula, Venkata Lokesh, et al., Human placenta and bone marrow derived MSC cultured in serum-free, b-FGF-containing medium express cell surface frizzled-9 and SSEA-4 and give rise to multilineage differentiation; 2007, Differentiation, vol. 75, pp. 279-291 (2007).

German Examination Report dated Dec. 14, 2012 from German Patent Application No. 10 2008 032 236.9 (two versions).

* cited by examiner

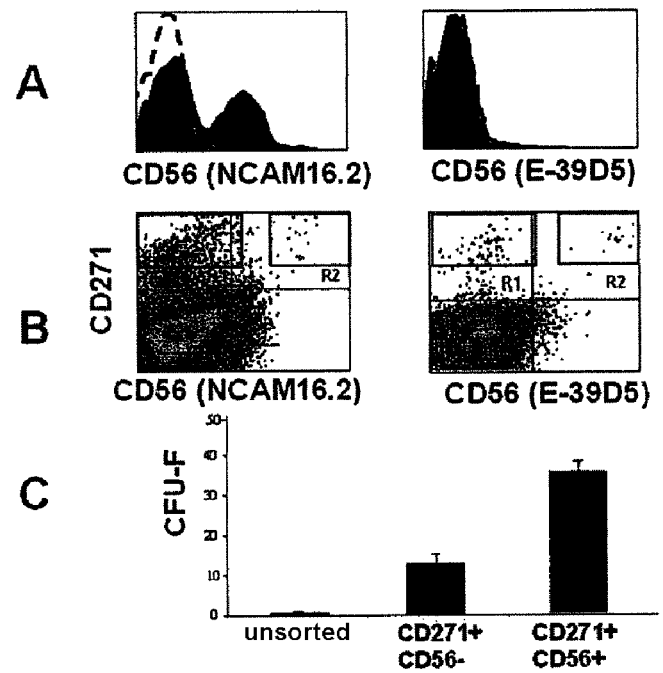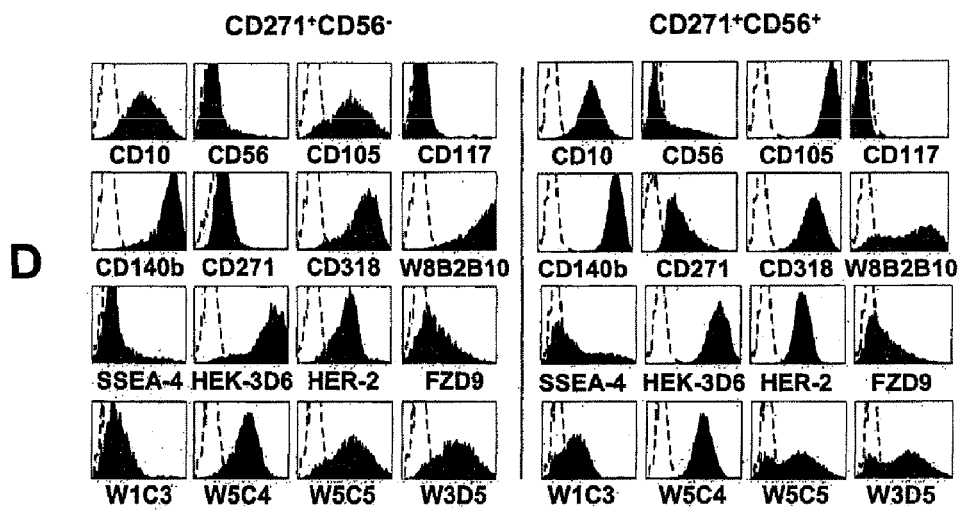
Fig. 1

Genes Upregulated in CD 56+ Cells

| Gene symbol | Gene name | gene access number | folding change |
|---|---|---|---|
| SFRP4 | secreted frizzled-related protein 4 | NM_003014 | 43.18 |
| ECRG4 | esophageal cancer-related gene 4 protein | NM_032411 | 21.06 |
| CPE | Carboxypeptidase E | NM_001873 | 15.34 |
| PDGFA | platelet-derived growth factor PDGF-A | X06374 | 13.41 |
| ETF1 | eukaryotic translation termination factor 1 | NM_004730 | 11.80 |
| CD163 | CD163 Antigen (CD163) | NM_004244 | 11.34 |
| T2BP | TRAF2 binding protein | NM_052864 | 10.99 |
| PH-4 | hypoxia-inducible factor prolyl-4-hydrolase | NM_177939 | 10.44 |
| LGALS13 | lectin, galactosidase-binding, soluble, 13, (galectin 13) | NM_013268 | 10.21 |
| TLR8 | Toll-like receptor 8 | NM_016610 | 8.39 |
| ITGA10 | Integrin, alpha 10 | NM_003637 | 8.36 |
| TJP1 | „Tight-junction"-Protein 1 (Zona occludens 1) | NM_003257 | 8.06 |
| DNAJB6 | DnaJ (Hsp40) homolog, subfamily B, member 6 | NM_058246 | 8.04 |
| LIMD1 | LIM domains containing 1 | NM_014240 | 7.905 |
| WIF1 | WNT inhibitory factor 1 | NM_007191 | 7.88 |
| KUB3 | Ku70 binding protein 3 | BC033881 | 7.04 |
| KLK4 | Kallikrein 4 | NM_004917 | 6.93 |
| UBE2B | Ubiquitin-conjugating enzyme E2B | BC001694 | 6.83 |

Fig. 5A

Genes Downregulated in CD 56+ Cells

| Gene symbol | Gene name | gene access number | folding change |
|---|---|---|---|
| LILRB2 | leukocyte immunoglobulin-like receptor, subfamily B | NM_005874 | -61.98 |
| ZNF212 | zinc finger protein 212 | NM_012256 | -38.64 |
| AREG | amphiregulin (Schwannoma-derived growth factor) | NM_001657 | -29.66 |
| HLA-DMB | main histocompatibility complex, Class II, DM beta | NM_002118 | -29.61 |
| SPON2 | spondin 2, extracellular matrix protein (SPON2) | NM_12445 | -23.59 |
| HLA-DRA | main histocompatibility complex, Class II, DR alpha | NM_019111 | -23.19 |
| GZMB | granzyme B (granzyme 2, cytotoxic T-lymphocyte-associated serine esterase 1) | NM_004131 | -21.20 |
| CSF2RA | colony-stimulating factor 2 receptor, alpha, low affinity (granulocytes-macrophages) | NM_172247 | -11.41 |
| FLJ12528 | Threonyl-tRNA-Synthetase | NM_025150 | -11.32 |
| HLA-DBP1 | main histocompatibility complex, Class II, DP beta 1 | NM_002121 | -11.29 |
| PLCB2 | Phospholipase C, beta 2 (PLCB2) | NM_004573 | -8.83 |
| MAPK1 | mitogen-activated protein kinase 1 | NM_138957 | -8.66 |
| COPG2 | "coatomer" protein complex, subunit gamma 2 | NM_012133 | -8.64 |
| NOTCH1 | Notch Homolog 1 | NM_017617 | -8.61 |
| MRPL23 | mitochondrial ribosomal protein L23 | NM_021134 | -7.77 |
| Septin6 | Septin 6 (SEPT6) | NM_015129 | -7.75 |
| GLRA2 | glycine receptor, alpha 2 | NM_002063 | -7.65 |
| BCL2A1 | BCL2-related protein A1 | NM_004049 | -7.14 |
| PANX1 | Pannexin 1 (PANX1) | NM_015368 | -6.68 |
| AF320072 | gastric cancer-related protein VRG118 | AF320072 | -6.68 |
| CD74 | CD74 antigen (invariant polypeptide of MHC, Class II antigen-associated) | NM_004355 | -6.65 |
| GDI1 | GDP dissociation inhibitor 1 | NM_001493 | -6.59 |
| CXCR4 | chemokine (C-X-C motif) receptor 4 | NM_003467 | -5.03 |

Fig. 5B

| Identity of clone | CD105 | CD166 | CD90 | CD73 | CD34 | CD45 | CD271 | CD56 | W8B2 | FZD9 | Cell count after 24-day culturing |
|---|---|---|---|---|---|---|---|---|---|---|---|
| CD56+ (C1) G11 | ++ | + | +++ | ++ | - | - | + | (+) | - | + | 450 X 10³ |
| CD56+ (C2) F7 | ++ | + | +++ | +++ | - | - | + | (+) | + | (+) | 450 X 10³ |
| CD56+ (C3) B6 | ++ | ++ | +++ | +++ | - | - | + | ++ | - | - | 75 X 10³ |
| CD56+ (C4) C4 | ++ | ++ | +++ | +++ | + | - | + | + | - | (+) | 12 X 10³ |
| CD56+ (C5) E4 | + | + | +++ | ++ | - | - | + | + | - | - | 12 X 10³ |
| CD56+ (C6) B12 | ++ | ++ | +++ | +++ | - | - | + | + | - | - | 1 X 10³ |
| CD56+ (C7) F10 | ++ | ++ | +++ | ++ | - | - | + | + | - | - | 3 X 10³ |
| CD56+ (C8) C1 | ++ | ++ | +++ | +++ | - | - | + | + | - | - | 7 X 10³ |
| CD56+ (C9) C6 | + | + | +++ | +++ | + | - | + | + | - | - | 9 X 10³ |
| CD56+ (C10) F6 | ++ | + | +++ | +++ | - | - | + | + | - | - | 5 X 10³ |
| CD56- (C11) B7 | ++ | + | +++ | +++ | (+) | - | + | + | - | + | 4 X 10³ |
| CD56- (C12) E9 | ++ | + | +++ | ++ | + | - | (+) | (+) | (+) | ++ | 100 X 10⁵ |
| CD56- (C13) C4 | ++ | + | +++ | +++ | - | - | (+) | - | + | + | 100 X 10⁵ |
| CD56- (C14) A9 | ++ | + | +++ | +++ | (+) | - | + | (+) | + | (+) | 50 X 10³ |
| CD56- (C15) E3 | ++ | + | +++ | ++ | (+) | - | (+) | + | - | (+) | 8 X 10³ |
| CD56- (C16) H9 | ++ | + | +++ | ++ | + | - | - | - | ++ | (+) | 6 X 10³ |

Fig. 6

ISOLATION AND/OR IDENTIFICATION OF STEM CELLS HAVING ADIPOCYTIC, CHONDROCYTIC AND PANCREATIC DIFFERENTIATION POTENTIAL

CROSS-REFERENCE TO RELATED APPLICATIONS

This application is a continuation of pending international patent application PCT/EP2009/004614, filed on Jun. 26, 2009 designating the U.S., which international patent application has been published in German language and claims priority from German patent application DE 10 2008 032 236.9, filed on Jun. 30, 2008. The entire contents of these priority applications are incorporated herein by reference.

BACKGROUND OF THE INVENTION

The present invention relates to the isolation and/or identification of stem cells having adipocytic, chondrocytic and pancreatic differentiation potential, and the use of these stem cells.

Mesenchymal stem cells (MSC), also known as mesenchymal stromal cells, are multipotent cells which have the ability under suitable in vitro and in vivo conditions to differentiate into various mesenchymal tissues. Thus for example they can differentiate into osteocytes, chondrocytes, adipocytes and myocytes and form bone, cartilage, fat and muscle tissue. In addition however, they can also differentiate into astrocytes, neurones, endothelial cells, hepatocytes, pancreas-like cells and pulmonary epithelial cells. Morphologically, they can be identified by their fibroblastoid phenotype and can be found in various adult and embryonic tissues in man, inter alia in the brain, bone marrow, umbilical cord blood, blood vessels, skeletal muscle, the skin, liver, gums and placenta.

MSC express a range of surface markers such as for example CD105 (endoglin, SH2), CD73 (ecto-5'-nucleotidase, SH3, SH4), CD166 (ALCAM), CD29 ($\beta$1 integrin), CD44 (H-CAM) and CD90 (Thy-1), some of which can also be found on endothelial and epithelial cells and on muscle cells. However, MSC can be distinguished from hematopoietic stem cells since MSC do not express the markers CD45, CD34 and CD133 specific for hematopoietic stem cells.

Mesenchymal stem cells have the property of rapidly and stably adhering to plastic or glass surfaces and forming colony-forming fibroblasts ("colony-forming units" (CFU-F)). However, the latter are heterogeneous in terms of their proliferation and differentiation capabilities.

Mesenchymal stem cells with a specific differentiation potential are of great interest in medicine and research: they can in particular be obtained from bone marrow, even from the elderly, have a high division rate and as aforesaid can differentiate into tissue cells of mesenchymal origin. Therefore for example in the context of stem cell therapies they could be used directly in the treatment of degenerative diseases of organs such as bone, cartilage, tendons, muscle, connective tissue, blood cells etc.

For the obtention or isolation of mesenchymal stem cells, unfractionated bone marrow cells which are cultured on plastic dishes are currently used as the starting material, the MSC are identified by their adhesion to the plastic surface, and the non-adhering hematopoietic cells are discarded from the sample. The cells obtained in this way are however less defined and differentiate not only into heterogeneous MSC populations, but also into osteoblasts, and/or osteoblast precursor cells, fat cells, reticular cells, macrophages and endothelial cells. Specific treatment of degenerative diseases of an organ with MSC without specific differentiation potential is thus difficult or impossible because of possible side-effects.

The isolation of mesenchymal stem cells with completely specific differentiation potential was not previously known or possible in the state of the art. However, as aforesaid, such isolation would have the great advantage that stem cells thus identified could be selectively used for the therapy/treatment of diseased, degenerated or damaged tissues into which the stem cells thus specifically isolated differentiate.

Thus for example cartilage damage could be treated by introducing specifically isolated mesenchymal stem cells with chondrogenic differentiation potential either directly in situ into the affected tissue, where they differentiate into chondrocytes and thus replace the damaged tissue (stem cell therapy). On the other hand, however, differentiation into chondrocytes in vitro can also be of interest if the aim is to obtain differentiated chondrocytes, for example for research/diagnosis/medicine.

Against this background there is great interest in mesenchymal stem cells with specific differentiation potential, in particular in order to use them in appropriate applications.

An object of the present invention is therefore to provide new ways whereby mesenchymal stem cells with a specific differentiation potential can be isolated.

SUMMARY OF THE INVENTION

According to the invention this and other objects are solved by a method for the isolation of stem cells with adipocytic, chondrocytic and pancreatic differentiation potential, the method comprising the step of using an antibody which binds to the TNAP (tissue non-specific alkaline phosphatase) antigen, or functional fragments of the antibody, in combination with an antibody which binds to CD56, or functional fragments of the antibody.

Further, the invention relates to stem cells isolated in this manner and to the use thereof, in particular in therapy.

The object underlying the invention is completely solved in this way. In their own experiments, the inventors of the present application were able to show that by use of the aforesaid antibody it is possible specifically to isolate mesenchymal stem cells which subsequently differentiate into chondrocytes, adipocytes or pancreas-like cells.

In particular, the inventors were able to show that said stem cells can be specifically isolated and/or identified via the TNAP antigen. On the basis of its occurrence, this isoform of the ectoenzyme "alkaline phosphatase" is also known as "liver/bone/kidney alkaline phosphatase". The three other isoforms are intestinal, placental, and placenta-like alkaline phosphatase. TNAP differs from the other isoforms through posttranslational modifications and through gene localization.

Hence for the first time a tool is provided with which mesenchymal stem cells which specifically differentiate can be obtained. This was not previously possible in the state of the art.

Thus on the basis of the new use and the new method, mesenchymal stem cells can be provided which in turn can for example advantageously be used in therapy and prophylaxis or else in diagnostics and research. Thus the stem cells thus isolated can in particular be used for treatment of diseases which are characterized by degenerated, injured or damaged tissue, for example in the context of stem cell therapy: for this, the stem cells isolated by means of the method according to the invention are transplanted into the affected tissue (for example also in conjunction with certain implants), and there differentiate into the corresponding tissue. The degenerated tissue is thereby regenerated and again capable of functioning.

In a further development of the method according to the invention, it is also preferable if the anti-TNAP antibody is selected from the group of:
the antibody W8B2 which is produced by a cell line deposited at the German Collection of Microorganisms and Cell Cultures under the No. ACC 2567,
functional fragments of the antibody W8B2 which is produced by a cell line deposited at the German Collection of Microorganisms and Cell Cultures under the No. ACC 2567, and
an antibody which binds to the same epitope as the antibody W8B2 which is produced by the cell line deposited at the German Collection of Microorganisms and Cell Cultures under the number ACC 2567.

The TNAP-specific antibody W8B2 has in other studies been found to be a marker for mesenchymal stem cells; thus in another invention by the applicant (DE 10 2006 043 625) the inventors were able to show that by means of the antibody W8B2 it is possible to isolate mesenchymal stem cells from primary tissue. However it was not previously known that with a combination of antibodies which are directed against TNAP and CD56, mesenchymal stem cells with entirely specific differentiation potentials could be obtained. The cells producing the antibody W8B2 were deposited at the German Collection of Microorganisms and Cell Cultures (DSMZ) in accordance with the Budapest agreement. The antibody was obtained by immunization of Balb/c mice with the retinoblastoma cell line WERI-RB-1. Originally the antigen recognized by the antibody W8B2 was called mesenchymal stem cell antigen-1; since then, however, the antigen recognized by antibody W8B2 has been identified as TNAP, hence the correct and official name of the antigen has been selected here.

In a preferred embodiment, the antibody binding to CD56 is selected from the group of:
the antibody 39D5 which is produced by the cell line deposited at the German Collection of Microorganisms and Cell Cultures under the number ACC 2930,
functional fragments of the antibody 39D5 which is produced by the cell line deposited at the German Collection of Microorganisms and Cell Cultures under the number ACC 2930,
an antibody which binds to the same antigen as the antibody 39D5 which is produced by the cell line deposited at the German Collection of Microorganisms and Cell Cultures under the number ACC 2930, and
an antibody which binds to the same epitope as the antibody 39D5 which is produced by the cell line deposited at the German Collection of Microorganisms and Cell Cultures under the number ACC 2930.

The antibody 39D5, which has also been deposited at the German Collection of Microorganisms and Cell Cultures in accordance with the Budapest agreement under the number ACC 2930, was obtained by immunization of Balb/c mice with the hematopoietic cell line KG-1a.

In one embodiment of the method according to the invention, it is preferable if, in addition to the combination of an anti-TNAP and an antibody directed against CD56, another antibody directed against CD271, or functional fragments of the antibody, is used.

Anti-CD271 antibodies in conjugated form are known in the state of the art and for example are available from Miltenyi Biotech, Bergisch Gladbach, Germany.

The CD271 antigen, which is also known as LNGFR ("low-affinity nerve growth factor receptor") or p75 NTR (neurotrophin receptor), belongs to the neurotrophin receptors with low affinity and to the superfamily of the tumor necrosis factor receptors. Originally CD271 (LNGFR) was described as a marker of cells of the nervous system, since CD271 (LNGFR) is found in the central and peripheral nervous system on autonomous and sensory neurones. In addition, CD271 is also expressed on oligodendrocytes, astrocytes and Schwann cells. Further, however, CD271 (LNGFR) is also found on certain MSC.

Herein, the term "functional fragments" as used in the application should be understood to mean substances which represent parts/sections of the disclosed antibodies and which still show and possess the functional properties, in particular the cell-binding or rather antigen-binding or epitope-binding properties, of the antibodies from which they are derived. At the same time these fragments can be used, either as such or in combination with other fragments; in the context of the present invention the latter should also for example be understood to mean modified W8B2 or 39D5 antibodies which have been adapted, for example humanized, for corresponding uses and applications in man.

The antibodies suitable for the purposes of the present invention are preferably monoclonal, and further antibodies directed against TNAP or CD56 can be obtained with the use of the antibodies W8B2 and 39D5. Instructions for preparation of monoclonal antibodies have been published by Köhler and Milstein ("Continuous cultures of fused cells secreting antibody of predefined specificity", Nature, (1975), 256:495-497).

Herein, however, fragments of such antibodies, such as for example Fab, F(ab)'$_2$ or scFv fragments, and other fragments such as CDR ("complementarity-determining region"), hypervariable region) are also regarded as antibodies in the sense and context of the present invention, as long as they possess their functionality, i.e. the specific binding properties possessed by the "whole" antibody from which they are derived. Such antibody fragments can for example also be produced recombinantly with the use of methods known in the state of the art.

Hence it also goes without saying that on the other hand the antibodies W8B2 and 39D5 can also be suitably humanized, and can be used in the context of the invention disclosed here for the applications and/or methods according to the invention, in particular also for stem cell therapy.

Humanized antibodies can for example be chimeric antibodies, in which the constant regions of the animal antibodies (for example from mouse or rabbit antibodies) are replaced by the corresponding regions of human antibodies, for example the Fc fragments (Sharon et al., Nature, (1984), 309:364-367). Alternatively, the CDR of the animal antibodies can also be combined with human antibodies; this process is known as antibody "reshaping". In a further, different method, human antibodies are produced in transgenic animals.

Further, in an application according to the invention, the antibodies, for example in humanized form, or functional fragments thereof, can be introduced into or applied onto suitable implantable medical devices, and be implanted into the patient to be treated together with the device at the site/tissue defects to be treated. Mesenchymal stem cells are then recruited to the site to be treated via the antibodies, and attach themselves to the implant, differentiate and thus form new tissue. Suitable medical devices here are any biocompatible implants, endoprostheses, for example stents etc., of any kind, which can be introduced either permanently or temporarily into the patient. The devices can optionally also consist of fully or partly absorbable materials, and as well as the antibodies contain further therapeutic active substances which are commonly used with implants/transplants to be introduced into a body.

As already mentioned above, the present invention also relates to a method for the isolation and/or identification of mesenchymal stem cells with adipocytic differentiation potential which comprises the following steps:

a) contacting a sample which contains mesenchymal stem cells with an antibody which binds to the antigen TNAP, or with functional fragments of the antibody, b) contacting the sample from step a) with an antibody which binds to CD56, or with functional fragments of the antibody, and c) isolation and/or identification of cells to which the antibody which binds to the antigen TNAP, or functional fragments of the antibody, but not the antibody which binds to CD56, or functional fragments of the antibody, has bound.

Thus with this embodiment of the method according to the invention stem cells which specifically differentiate into adipocytes can be obtained. These in turn can be used for quite specific purposes, whether in research or medicine.

Further, the present invention relates to a method for the isolation and/or identification of mesenchymal stem cells with chondrocytic or pancreatic differentiation potential, wherein the method comprises the following steps:

a) contacting a sample which contains mesenchymal stem cells with an antibody which binds to the antigen TNAP, or with functional fragments of the antibody, b) contacting the sample from step a) with an antibody which binds to CD56, or with functional fragments of the antibody, and c) isolation and/or identification of cells to which both the antibody which binds to the antigen TNAP, or functional fragments of the antibody, and also the antibody which binds to CD56, or functional fragments of the antibody, have bound.

With this embodiment of the method according to the invention, stem cells which have a chondrogenic or pancreatic differentiation potential can be identified and/or isolated. The stem cells thus obtained can then either be used directly in the context of stem cell therapy (autologous or allogenic therapy), where they differentiate in situ into chondrocytes or pancreas-like cells, and can thus regenerate degenerated or damaged cartilage tissue or pancreatic tissue.

On the other hand, the mesenchymal stem cells with chondrogenic/pancreatic differentiation potential obtained by the method according to the invention can also firstly be differentiated into chondrocytes/pancreas-like cells in vitro, and then be used for the treatment of diseased or degenerated tissue.

In particular in recent years autologous chondrocyte transplantation has developed into a preferred intervention for the treatment of (articular) cartilage defects of disk and knee, whereby the hyaline cartilage should be recreated. For this, samples are taken from the patient by arthroscopy from an undamaged joint part, and the cartilage cells contained therein are grown on special matrices in the laboratory. The tissue thereby formed, i.e. the new cartilage, is then transplanted into the diseased/degenerated joint by a tissue-conserving second operation.

With the method according to the invention it is now for the first time possible to isolate stem cells with for example chondrogenic differentiation potential selectively from the tissue of a patient and to achieve rapid, efficient and specific growth of chondrocyte tissue for subsequent transplantation into the sample donor (autologous transplantation) or another recipient (allogenous transplantation).

Also, in the method according to the invention it is preferable if the anti-TNAP antibody used in step a) is selected from the group of:

the antibody W8B2 which is produced by the hybridoma cell line deposited at the German Collection of Microorganisms and Cell Cultures with the No. ACC 2567, functional fragments of the antibody W8B2, and antibodies which bind to the same epitope as the antibody W8B2 which is produced by the hybridoma cell line deposited at the German Collection of Microorganisms and Cell Cultures with the No. ACC 2567.

Further, in a further development of the method according to the invention, it is preferable if the antibody binding to CD56 used in step b) is selected from the group of:

the antibody 39D5 which is produced by the hybridoma cell line deposited at the German Collection of Microorganisms and Cell Cultures with the No. ACC 2930, functional fragments of the antibody 39D5, and antibodies which bind to the same epitope as the antibody 39D5 which is produced by the hybridoma cell line deposited at the German Collection of Microorganisms and Cell Cultures with the No. ACC 2930.

Also, in a further embodiment of the method according to the invention, it is preferable if it comprises the further step c'):

c') contacting the sample from step b) with an antibody which binds to CD271, or with functional fragments of the antibody.

Here in the method according to the invention it can be provided according to the invention that the steps a), b) and c') are performed simultaneously, one after another or in reverse order.

The inventors have established in their own experiments that with the use of the antibodies W8B2 and 39D5 in a method for the isolation/identification of mesenchymal stem cells, selective enrichment of mesenchymal stem cells with chondrogenic/adipocytic or pancreatic differentiation potential could be obtained.

The present invention further relates to a method for treating an individual in need thereof with stem cells which were isolated and/or identified with the method according to the invention. The stem cells which have been isolated and/or identified with the method according to the invention may also be used in diagnosis or research, or methods related to diagnosis or research.

For this, in one embodiment it is preferable if the stem cells obtained with the method according to the invention are used in a method for the specific generation of chondrocytes, adipocytes and pancreas-like cells, to be precise in vivo or in vitro.

Further, in a further embodiment it is preferable if the stem cells isolated and/or identified with the method according to the invention which and were differentiated into chondrocytes, adipocytes and pancreas-like cells, are used in a method for the therapy and/or prophylaxis of degenerated or susceptible tissues.

In particular it is preferable if the stem cells obtained with the method according to the invention are used in a method for the therapy/treatment and/or prophylaxis of cartilage and/or bone damage, degeneration or diseases, in particular of the knee and disks, or for rheumatoid arthritis. Rheumatoid arthritis is an autoimmune disease, and even in this disease the application of stem cells for tissue replacement (i.e. for so-called "tissue repair") can be used.

The invention further relates to a pharmaceutical composition and a kit which comprises a combination of the antibody W8B2 which is produced by the hybridoma cell line deposited at the German Collection of Microorganisms and Cell Cultures with the No. ACC 2567, or antigen-binding fragments thereof, and the antibody 39D5 which is produced by the hybridoma cell line deposited at the German Collection of Microorganisms and Cell Cultures with the No. ACC 2930, or antigen-binding fragments thereof.

The invention further relates to a pharmaceutical composition containing stem cells which were isolated and/or identified according to the method according to the invention, and at least one pharmaceutically acceptable carrier and/or additive, and if necessary therapeutically active substances.

Herein "pharmaceutically acceptable carrier and/or additives" is understood to mean any substance/composition for administration in pharmacy in connection with to a patient, which does not adversely influence the activity of the cells/antibodies, and/or can support or facilitate the use of the pharmaceutical composition.

Herein "therapeutically active substance" is understood to mean any substance which is used for the purposes of treatment or improvement of the disease picture of a patient.

The pharmaceutical compositions can be administered systemically, i.e. for example orally, subcutaneously, intravenously, rectally, parenterally, intramuscularly, intraperitoneally, transdermally, or topically, and the mode of administration will depend on the nature of the disease, the disease picture, and the condition of the patient. Likewise, the administration can be effected repeatedly or singly, and in the former case the administration can take place once or several times a day, and/or over a longer period.

In addition to the active substances, the pharmaceutical composition can also contain buffers, diluents and/or additives. Suitable buffers include for example Tris HCl, glycine and phosphate, and suitable diluents include for example aqueous NaCl solutions, lactose or mannitol. Suitable additives include for example detergents, solvents, antioxidants and preservatives. There is for example a review of such additional ingredients in A. Kibbe: "Handbook of Pharmaceutical Excipients", $3^{rd}$ Ed., 2000, American Pharmaceutical Association and Pharmaceutical Press.

It goes without saying that the aforesaid features and those still to be explained below can be used not only in the particular combinations stated, but also in other combinations or alone, without departing from the scope of the present invention.

BRIEF DESCRIPTION OF THE DRAWINGS

The invention is explained in more detail in the following description and the appended figures.

These show:

FIG. 1 Characterization of the CD56+ bone marrow cells. (A) The CD56 epitope NCAM16.2, but not that of 39D5, is expressed on peripheral blood NK cells. (B) The CD56 epitopes NCAM16.2 and 39D5 are expressed on a rare CD271+ bone marrow subset. (C) CD271+CD56+ and CD271+CD56− bone marrow cells are clonogenic. CFU-F, derived from 500 FACS-sorted cells, were stained and assessed as described. The data represent the mean value of the CFU-F numbers of three different experiments (*p<0.01). (D) Expression of selected markers on cultured CD271+ CD56− and CD271+CD56+ MSC.

Triply stained bone marrow cells were restricted to the CD271+ subset and analyzed for the coexpression of CD56 and selected markers.

(A) Representation of FSC against CD271-APC.

(B) Representation of CD56 against the markers shown on $CD271^{bright}$-restricted cells.

(C) Representation of CD56 against TNAP (W8B2) on $CD271^{bright}$ cells. The sorting windows are designated as R2 and R3.

(D) CFU-F numbers, derived from 1,000 FACS-sorted BM TNAP+CD56− and TNAP+CD56+ cells or 100,000 unfractionated bone marrow cells. The resulting CFU-F were stained and assessed 12 days after culturing, and normalized to 1,000 plated out cells (p<0.01).

(E) Morphology of TNAP+CD56− and TNAP+CD56+ bone marrow cells. The subsets were sorted, cytocentrifuged and stained with May-Grünwald-Giemsa solution; they were then assessed with a Zeiss Axiovert 200 microscope.

Figure 3:
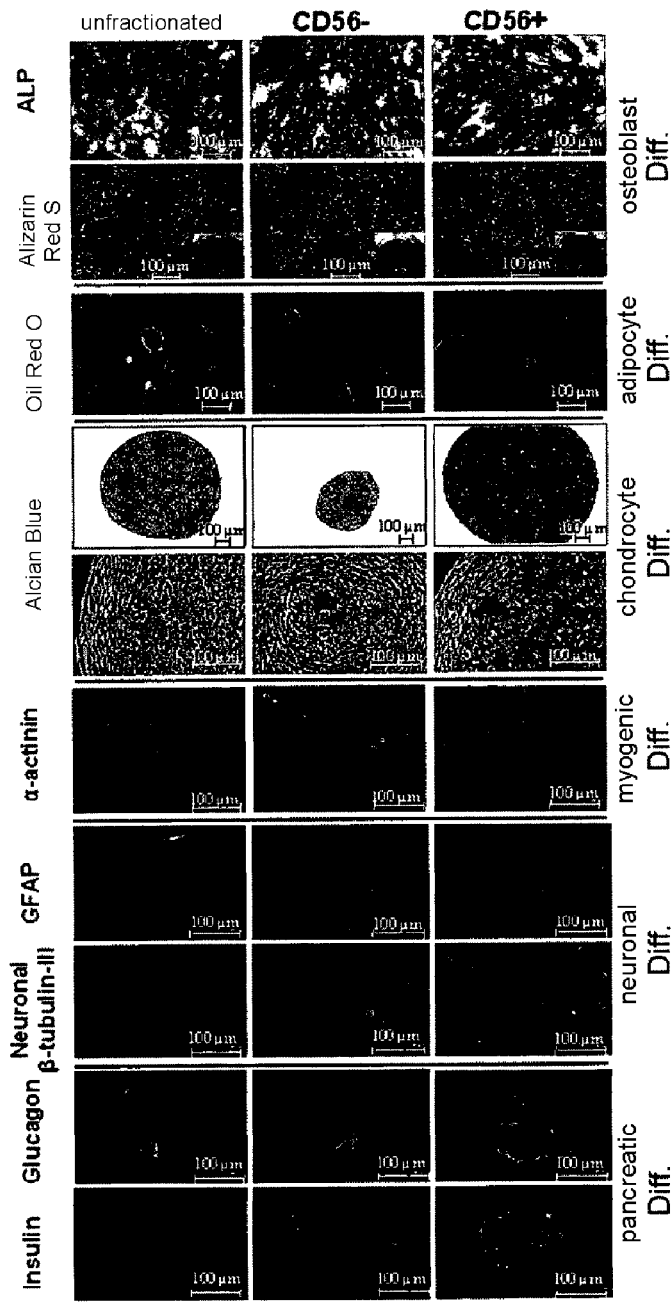

FIG. 3 Differentiation potential of MSC which are derived from sorted TNAP+CD56− and TNAP+CD56+ bone marrow cells.

Cells triply stained with CD271, TNAP (W8B2) and CD56 were sorted and cultured as described. Expanded MSC were induced for osteogenic, adipogenic, chondrogenic, myogenic, neurogenic and pancreatic differentiation and stained as described. The resulting cells were photographed with a Zeiss Axiovert 200 microscope.

Figure 4:
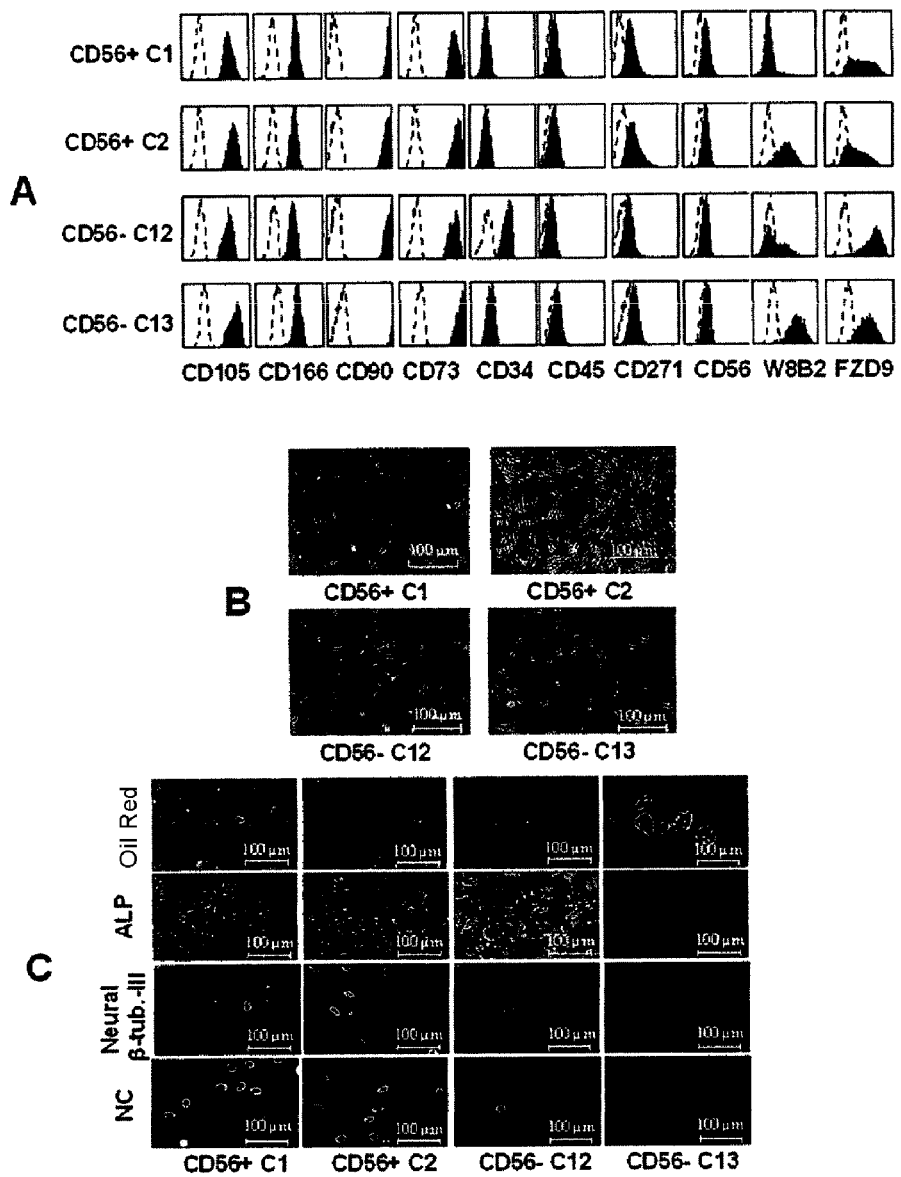

FIG. 4 Phenotype and differentiation capability of MSC derived from individual cells. (A) Bone marrow cells, triply stained with CD56-FITC. TNAP-PE and CD271-APC were limited and sorted as described for FIG. 2C. The individual cells were sorted in 96-well plates and cultured for 12 days. The MSC colonies formed were transferred into T-25 bottles and cultured for a further 12 days; they were then stained with the relevant antibodies. (B) Morphology of the TNAP+ CG56+-derived MSC clones C1 and C2 and the TNAP+ CD56' derived clones C12 and C13. (C) osteogenic, adipogenic and neuronal differentiation potential of the MSC derived from individual TNAP+CD56" and TNAP+CD456+ bone marrow cells.

FIG. 5 Microarray gene expression analysis of the CD271+ CD56− and CD271+CD56+ bone marrow cells.

The microarray analysis was performed using RNA from 10,000 sorted CD271+CD56− and CD271+CD56+ bone marrow cells. (A) Upregulated genes in the CD271+CD56+ population compared to the CD271+CD56− fraction. (B) Downregulated genes in the CD271+CD56+ population compared to the CD271+CD56− fraction.

FIG. 6 Table 2: Phenotype and proliferation of the MSC clones (C1 to C16) derived from individual TNAP+CD56− and TNAP+CD56+ bone marrow cells.

"+++" means>100 mean fluorescent intensity (MFI); "++" means 10-100 ΔMFI; "+" means 3-10 ΔMFI; "(+)" means 1-3 ΔMFI; "−" means negative staining.

Figure 7:
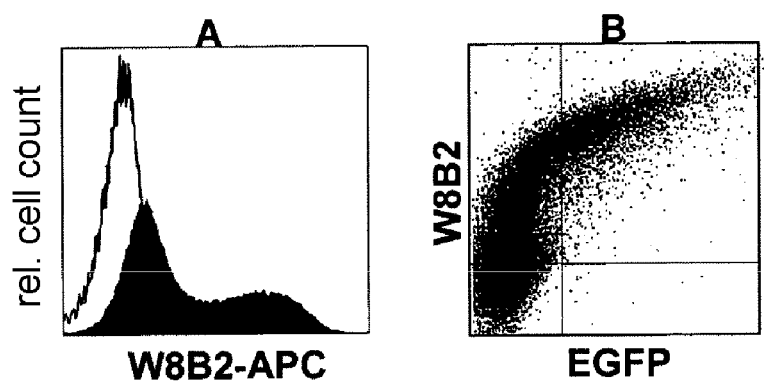
Figure 8:
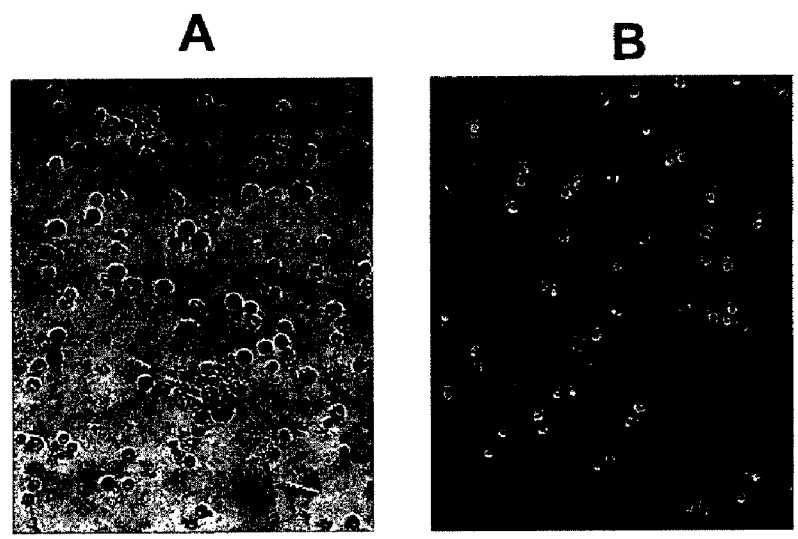

FIG. 7 Transfection of HEK-293 cells with TNAP:

HEK-293 cells transfected with the coding sequence of TNAP/ALPL (Homo sapiens alkaline phosphatase, liver/bone/kidney (ALPL)), labeled with W8B2-APC; as well as TNAP (W8B2 antigen) (A), the cells also express the reporter gene GFP (B); and FIG. 8 Bone marrow cells sorted via the TNAP-specific antibody W8B2, stained for the detection of the alkaline phosphatase: W8B2-positive cells (A); W8B2-negative cells (B).

DESCRIPTION OF PREFERRED EMBODIMENTS

Examples

Materials and Methods
Isolation of Bone Marrow Cells and Mononuclear Peripheral Blood Cells Bone marrow ("BM") was obtained from the femoral shafts of patients at the Trade Association Clinic who had been given artificial hip joints. Peripheral blood (PB) from healthy donors was obtained from the Institute of Transfusion Medicine at the Tübingen University Clinic. Mononuclear cells from the bone marrow (BMMNC) and mononuclear cells from the blood (PBMMC) were isolated by Ficoll density gradient fractionation, and the remaining erythrocytes were lysed in an ammonium chloride solution.

Culturing of Primary Cells

The Ficoll-separated and FACS-enriched bone marrow cells were cultured as follows: $2\times10^7$ unfractionated or $1\times10^4$ sorted $TNAP^+CD56^+$ and $TNAP^+CD56^-$ bone marrow cells were cultured in gelatin-coated T-75 or T-25 culture bottles in the presence of 20 ml or 6 ml of Knockout™ replacement medium (Invitrogen, Karlsruhe, Germany) and 5 ng/ml of recombinant human fibroblast growth factor (rh-bFGF; Cell-Systems, Remagen, Germany). After culturing for 3 days, the non-adhering cells were removed and fresh medium was added. The adherent cells were cultured until they reached 90% confluence.

Colony-Forming Fibroblast Assay (CFU-F)

CFU-F assays were performed by plating out either $1\times10^5$ unselected or 500-5,000 FACS-selected BMMNC into gelatin-coated T-25 bottles which contained Knockout™ medium and 5 ng/ml of rh-bFGF. After culturing for twelve days, the adherent cells were washed twice with PBS, fixed for five minutes at room temperature with methanol (Sigma-Aldrich), air-dried and stained with Giemsa solution (Merck, Darmstadt, Germany). CFU-F colonies were counted macroscopically. The size of the colonies was between 1 and 8 mm diameter.

Differentiation of the MSC

Osteoblast and Adipocyte Differentiation

MSC which were derived from sorted $TNAP^+CD56^\pm$ or unfractionated BM cells were cultured in NH OsteoDiff or NH AdipoDiff medium (Miltenyi Biotec, Bergisch Gladbach, Germany). For this, $2\times10^4$ (osteogenesis) or $4\times10^4$ (adipogenesis) MSC were cultured in 24-well plates (Falcon, Heidelberg, Germany). After 12 days in culture in NH Osteo-Diff medium, the cells were fixed with methanol ($-20°$ C., 5 mins). The alkaline phosphatase activity in osteoblasts was determined using the FAST™ BCIP/NBT substrate (Sigma-Aldrich). The calcium deposition in fixed cells (4% PFA, 15 mins) was analyzed after staining with 2% Alizarin Red (Merck) for 10 mins at room temperature. The formation of adipocytes was investigated after 25 days in culture in NH AdipoDiff medium and after staining of the methanol-fixed cells for 45 minutes at room temperature with Oil Red O dye (Sigma-Aldrich). Pictures were taken using an Axiovert 40C microscope (Carl Zeiss GmbH, Göttingen, Germany).

Chondrogenic Differentiation $4\times10^5$ MSC were cultured for 4 hours at 37° C. in 20 µl of incomplete chondrogenic induction medium (PAA, Pasching, Austria) which contained 1% ITS supplement (Sigma-Aldrich), 175 µM L-ascorbic acid (Sigma-Aldrich), 350 µM L-proline (Sigma-Aldrich) and 100 nM dexamethasone (Sigma-Aldrich). After incubation, 400 µl of the complete chondrogenic induction medium which was supplemented with 10 ng/ml of TGF-$\beta_3$ (Sigma-Aldrich) was added. The resulting cell pellets were cultured for 3 weeks, fixed with 4% PFA, embedded in paraffin and cut into 5 µm thick sections. The dried and deparaffinized sections were incubated for 45 mins at room temperature with Alcian Blue solution (Merck), washed in 3% acetic acid, embedded and photographed with a Zeiss Axiovert 200 microscope.

Myogenic Differentiation $5\times10^5$ MSC were cultured for 7 days in vessels with very low adherence in DMEM High Glucose (Invitrogen) which was supplemented with 100 µM β-mercaptoethanol. The resulting clusters were placed in gelatin-coated 24-well vessels for 21 to 28 days, the resulting cells fixed with 4% PFA (45 mins, at room temperature), and permeabilized over 20 mins with 0.1% Triton X-100/PBS. The cells were labeled overnight at 4° C. with rabbit anti-human antibodies against actin of the smooth musculature (SMA) (Spring Bioscience, Freemont, Calif., USA) and with a mouse anti-human antibody against sarcomere actinin (anti-alpha-actinin) (Sigma-Aldrich). After the washing, the cells were stained with Cy3-conjugated goat anti-rabbit IgG (Jackson Immuno Research) or Alexa Fluor488-conjugated goat anti-mouse IgG (Invitrogen) and 0.4 µg/ml of DAPI.

Neuronal Differentiation $3.5\times10^4$ MSC were cultured for 6 days in 800 µl NeuroCult® NS-A proliferation medium (CellSystems), and then for 7 days in the NeuroCult® NS-A differentiation medium (CellSystems). The cells were fixed with 4% PFA and permeabilized with 0.3% Triton-X-100/PBS (Sigma-Aldrich), to be precise this before they were incubated overnight with rabbit anti-human antibody against gliafibrillar acid protein (GFAP) or the mouse anti-human antibody against neuronal class III β-tubulin (each from CellSystems). After washing with 0.1% BSA/TBS/Tween-20 (Sigma-Aldrich), the cells were stained with the Cy3-conjugated secondary pig anti-rabbit antibody (30 mins at room temperature, Jackson Immuno Research, Cambridge, Great Britain), or with the Alexa Fluor®488-conjugated goat anti-mouse IgG secondary antibody (Invitrogen) and 0.4 µg/ml of DAPI.

Pancreatic Differentiation $5\times10^5$ MSC were plated out into 6-well vessels with very low adherence (Costar; CellSystems), and cultured for 4 days in MEM which contained 1 mM monothioglycerol, 15% ES-Cult FBS and 4.5 g/l of DMEM High Glucose (CellSystems). The resulting cell clusters were then cultured for 6 days in 6-well adherent plates (Falcon) in ITS-supplemented, serum-free medium (CellSystems). After transfer into poly-L-ornithine-coated 24-well plates, the cells were cultured for 6 days in a pancreatic proliferation medium (CellSystems) which contained N2-A and B27 supplement substances, and 25 ng/ml of rh-bFGF, and then for a further 6 days in an rh-bFGF-free pancreatic differentiation medium (CellSystems) containing 10 mM nicotinamide. After washing, the cells were fixed with 4% PFA, permeabilized with 70% ethanol and incubated with a blocking buffer which contained 0.25% Triton X-100 and 2% FBS. Next, they were labeled overnight with a polyclonal rabbit anti-human glucagon antibody (1:75 dilution, Dako Cytomations, Glostrup, Denmark) or with a polyclonal rabbit anti-human insulin antibody (1:200 dilution, Anta Cruz Biotechnology) and stained with a secondary goat anti-rabbit IgG-Cy³ (Millipore, Schwalbach, Germany) and 0.4 µg/ml of DAPI.

Generation of the MSC-Reactive Monoclonal Antibodies W8B2 and 39D5

The monoclonal antibody W8B2 (IgG1, specificity for hTNAP) was obtained by immunization of 6 to 8-week old female Balb/c mice (Charles River WIGA, Sulzfeld, Germany) with the retinoblastoma cell line WERI-RB-1. The antibody 39D5 (IgG1, CD56) was obtained by immunization with the hematopoietic cell line KG-1a.

Immunofluorescence Analysis and Cell Sorting
Antibodies

The following antibodies were used: 97C5 (CD10), 46A11 (CD13), 39D5 (CD56), 1G2C2 (CD105), 104D2 (CD117), W6B3C1 (CD133), 28D4 (CD140b), 67D2 (CD164), CUB1 (CD318, CDCP1), 24D2 (CD340, HER-2), W3C4E11 (CD349, frizzled-9), HEK-3D6 (unknown), W1C3 (unknown), W5C4 (unknown), W5C5 (unknown), W3D5 (unknown) and W8B2B10 (TNAP). CD34-PE (clone 8G12), CD45-PE (clone HI30), CD56-FITC (clone NCAM16.2), CD56-PE (clone NCAM16.2), CD90-APC (5E10), CD63-PE (clone H5C6), CD73-PE (clone AD2) and HLA-DR-PE (clone TÜ36) were bought from Becton Dickinson (Heidelberg, Germany). The SSEA-4-reactive antibody MC-813-70 was purchased from Chemicon (Hampshire, Great Britain). CD271-APC (clone ME20.4-1.H4) was purchased from Miltenyi Biotec. CD105-PE (clone SN6) was purchased from eBioscience Inc. (San Diego, Calif., USA). CD166-PE was obtained from Dr. Gene Lay (BioLegend, San Diego, Calif., USA).

Immunofluorescent Staining after blocking and specific bindings with 10 mg/ml of polyglobin (10 mins, 4° C.), the cells were incubated for 15 mins with either 20 μl of antibodies or 10 μl of fluorochrome-conjugated antibodies. The cells stained with the conjugates were washed twice, suspended in 200 μl of FACS buffer and used for the flow cytometry. The cells which were labeled with the antibodies were stained for 15 mins with 20 μl of an F(ab)$_2$ fragment of the R-phycoerythrin (PE)-conjugated goat anti-mouse antibody (Dako Cytomations, Glostrup, Denmark), washed twice and analyzed by flow cytometry. For the multicolor staining, the cells were incubated for 15 mins with 10 μl of an anti-CD56-FITC and anti-CD271-APC and/or said PE conjugate. After washing, the cells were used for the flow cytometry. For combined indirect and direct staining, the cells were firstly labeled with the indirect antibody, and then stained for 15 mins with 20 μl of 1:25 diluted goat anti-mouse secondary antibody. The free binding sites of the secondary antibody were blocked by incubation of the cells with 20 μl of a mouse IgG polyclonal antibody (0.05 μg/ml, Southern Biotech, Birmingham, Ala.) for 25 mins before they were counterstained with CD271-APC and/or CD56-FITC. After a washing step the cells were analyzed by flow cytometry.

Flow Cytometry Analyses and Cell Sorting

The cells were sorted on an FACSAria cell sorter (Becton Dickinson), or analyzed with an FACSCantoII flow cytometer (Becton Dickinson). The data were analyzed using the FCS Express software (De Novo Software, Ontario, Canada). The single cell sorting in 96-well plates was performed using the ACDU appliance.

MACS Separation

In selected experiments, the bone marrow cells were pre-sorted by MACS (Miltenyi Biotec) using CD271-APC and anti-APC beads. The separations were performed according to the manufacturer's recommendations.

Gene Chip Analysis of the Sorted Cells

Ten thousand TNAP$^+$CD56$^-$ and TNAP$^+$CD56$^+$ cells were used for a commercial gene chip analysis (Miltenyi Biotec) to perform an oligo microarray of the human whole genome (Agilent Technologies, Böblingen, Germany). The amplified cDNAs were quantified using an ND-1000 spectrophotometer (NanoDrop Technologies Inc., Wilmington, Del.). 250 ng of the library PCR were used as template for Cy3 and Cy5 labeling. The samples were hybridized for 17 hours at 65° C. on the microarray from Agilent according to the manufacturer's instructions. The scanning of the gene chip and the data analysis were performed using the Luminator software (Miltenyi Biotec).

Results

The monoclonal antibody 39D5 recognizes an epitope of CD56 which is not expressed on the surface of peripheral blood (PB)-derived NK cells. A comparative flow cytometry analysis showed that only the commercially available CD56-specific antibody NCAM16.2, but not the monoclonal antibody 39D5, reacted with 20±% of the PB cells (FIG. 1A). However, both antibodies reacted with a small subpopulation of BM CD271$^{bright}$ cells (FIG. 1B). Simultaneous staining of BM cells with 39D5 and NCAM16.2 showed that both antibodies detected the same CD271$^{bright}$ population.

The CD271$^{bright}$ CD56$^+$ Population is Enriched for CFU-F

To determine the clonogenic potential of sorted CD56$^+$ and CD56$^-$ subsets, CFU-F assays were performed. FIG. 1C shows a threefold (±0.8) enriched efficiency of CD271$^{bright}$CD56$^+$ cells compared to CD271$^{bright}$CD56$^-$ cells and 180-fold (±52) enrichment of CFU-F compared to the unfractionated BM cells. The enrichment was independent of the CD56 epitope analyzed. Interestingly, the CD271$^{bright}$CD56$^+$ cells not only achieved higher colony counts (38/500 compared to 12/500 plated cells), but were also 2- to 4-fold enriched in the very large colonies (>100 cells/colony).

Phenotype of the MSC Which Were Derived From the Sorted CD271$^{bright}$CD56$^±$ BM Cells CD271$^{bright}$CD56$^+$ and CD271$^{bright}$CD56$^-$ cells were separated by FACS, cultured in gelatin-coated bottles in the presence of a serum replacement medium (n=3), stained with the stated antibodies and analyzed by flow cytometry. FIG. 1D shows that CD10, CD140b, CD318, HER2 (CD340) and frizzled-9 (CD349), just like the antibody-defined antigens W1C3, W5C4, W5C5 and W3D5, were similarly expressed on MSC which were derived from both fractions. CD271, SSEA-4 and CD56 were most densely expressed on CD271$^{bright}$CD56$^+$-derived MSC, whereas TNAP (W8B2 antigen) expression was more pronounced on CD271$^{bright}$CD56$^-$-derived MSC. In contrast to primary MSC (FIG. 2B), cultured MSC expressed CD166 and CD318 de novo, and downregulated the expression of CD271.

Gene Expression Analysis of Primary CD271$^{bright}$CD56$^-$ and CD271$^{bright}$CD56$^+$ Bone Marrow Cells A microarray analysis of the whole genome of 10,000 sorted bone marrow cells was performed in order to compare the expression profile of CD271$^{bright}$CD56$^-$ and CD271$^{bright}$CD56$^+$ bone marrow cells. CD271$^{bright}$CD56$^+$ cells showed 11- to 43-fold increased expression of secreted frizzle-related protein 4, esophageal cancer-related gene 4 protein, carboxypeptidase E, platelet-derived growth factor A, eukaryotic translation termination factor 1 and CD163 (FIG. 5A). In contrast to this, the genes which coded for the leukocyte immunoglobulin-like receptor subfamily B, for zinc finger protein 212, amphiregulin, HLA class II DM beta, spondin 2 and HLA class II DR alpha were expressed with 62- to 23-fold decreased levels in this subset (FIG. 5B), which indicates a high diversity of the gene expression profile in this subset.

Phenotype of the CD271$^{bright}$CD56$^±$ Bone Marrow Cells

Figure 2:
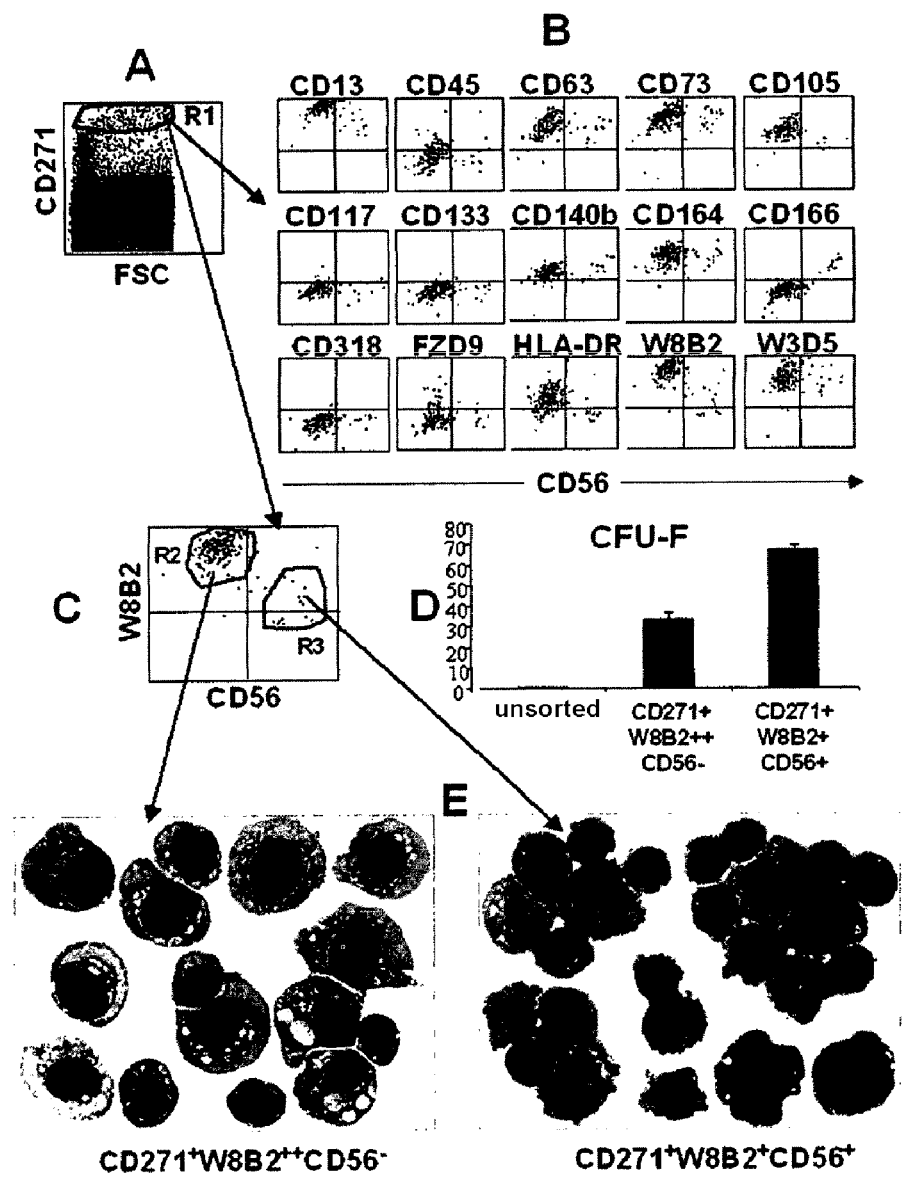
FIG. 2 Phenotype and morphology of $CD271^{bright}TNAP^+CD56^-$ and $CD271^{bright}TNAP^+CD56^+$, derived from the bone marrow.

To compare the expression profiles of the surface markers on CD271$^{bright}$CD56$^+$ and CD271$^{bright}$CD56$^-$ cells, the bone marrow cells were triply stained with anti-CD271, anti-CD56 and a range of test antibodies and limited to the CD271$^{bright}$ population (FIG. 2A, window R1). FIG. 2B shows that CD63, CD73, CD140b, CD164 and the W3D5 antigen were expressed at a similar level on both subsets, whereas CD45, CD117, CD133 and CD318 were negative. In contrast to this, CD271$^{bright}$CD56$^+$ cells expressed CD13, CD105, frizzled-9 (CD349), HLA-DR and TNAP (W8B2 antigen) at a reduced level, whereas CD166 was found exclusively on these cells. The fact that CD166 expression is lacking on the majority of the primary MSC was surprising, since it is well known that cultured MSC express high levels of CD166. The tumor antigen CDCP1 (CD318) was also negative on primary CD271$^{bright}$CD56$^-$ and CD271$^{bright}$CD56$^+$ cells (FIG. 2B), but strongly expressed in cultured MSC (FIG. 1B).

Clonogenic Capability of TNAP$^+$ CD56$^+$ Bone Marrow Cells

With the present results, it could be shown that TNAP is expressed at a high level on CD271$^{bright}$CD56$^-$ cells and at a lower level on CD271$^{bright}$CD56$^+$ cell subsets (FIG. 2A). In order to study the clonogenic capability of these subsets, the cells were fractionated with the windows R2 and R3 (FIG. 2C). Defined cell numbers were placed in culture bottles, and the resulting CFU-F were counted after culturing for 12 days. FIG. 2D shows that TNAP$^+$CD56$^+$ cells led to a 2 (±0.4) times higher CFU-F count than the TNAP$^+$CD56$^-$ cells. Giemsa staining showed that the TNAP$^+$CD56$^-$ cells contained a large and bright cytoplasm with vacuoles, whereas the TNAP$^+$CD56$^+$ cells contained a smaller cytoplasm with basophilic corpuscles (FIG. 2E).

Differentiation Capability of MSC Derived from TNAP$^+$ CD56$^±$ Cells

For the differentiation assays, unfractionated or sorted TNAP$^+$CD56$^-$ and TNAP$^+$CD56$^+$ cells were expanded until they had undergone 9 to 10 cell divisions. A defined number of the resulting MSC were then induced in order to differentiate into cells of the osteogenic, adipogenic, chondrogenic, myogenic, neuronal and pancreatic lines.

Osteoblastic Differentiation

Culturing of MSC which were derived from sorted cell subsets in a suitable medium led to the appearance of 95±5% (CD56$^+$) and 70±5% (CD56) of alkaline phosphatase-positive cells (FIG. 3). In contrast to this, MSC which were derived from the unfractionated bone marrow cells led to only 35%±5% of alkaline phosphatase-positive cells. Alizarin Red S staining could be observed in all osteoblast fractions. However, the quantity of calcium deposition in the osteoblasts which were derived from the unfractionated cells was twice as high.

Adipocyte Differentiation

Culturing of unfractionated and TNAP$^+$CD56$^-$-derived MSC in adipocyte differentiation medium led to the appearance of Oil Red O-incorporating adipocytes. In contrast to this, TNAP$^+$CD56$^+$-derived MSC were not able to form adipocytes (FIG. 3). TNAP$^+$CD56$^-$ MSC showed a 5±0.5-fold rise in Oil Red O-positive adipocytes, compared to unfractionated cells. Hence the capacity for adipocyte differentiation is restricted to the TNAP$^+$CD56$^-$ subset.

Chondrogenic Differentiation

In order to analyze the potential for chondrogenic differentiation, MSC which were derived from the fractionated and unfractionated cells were cultured in a suitable medium and the resulting cell pellets were stained with Alcian Blue. Although a chondrogenic differentiation was detected in both fractions, pellet sections from TNAP$^+$CD56$^+$ cells were 5 (±1.6) times larger than those from TNAP$^+$CD56$^-$ cells (FIG. 3). In addition, viable chondrocytes were detected almost exclusively in the TNAP$^+$CD56$^+$ subset, whereas TNAP$^+$CD56$^-$ pellets mainly contained apoptopic cells. MSC from unfractionated cells led to heterogeneous pellet sizes, but generally with fewer viable cells. These data make it clear that effective chondrogenesis is restricted to the TNAP$^+$CD56$^+$ MSC subset.

Myogenic Differentiation

Culturing of the TNAP$^+$CD56$^±$-derived MSC in a medium which was intended for the differentiation into cells of the striated musculature led to the occurrence of an α-actin staining specific for the striated musculature in cells of all fractions (FIG. 3). In contrast to this, the marker SMA specific for the smooth musculature was negative in all fractions. Undifferentiated MSC exhibited very weak α-actin staining.

Neuronal Differentiation

MSC which were cultured in a neuronal differentiation medium were stained for GFAP and β-tubulin III. FIG. 3 shows marked staining of cells which were derived from unfractionated and from TNAP$^+$CD56$^+$ and TNAP$^+$CD56$^-$-derived MSC. In undifferentiated MSC or in differentiated cells which were labeled with isotype-specific control antibodies, no staining was observed.

Pancreatic Differentiation

Culturing of MSC in a pancreatic differentiation medium led to a glucagon- and insulin-staining of pancreas-like islets in cells of all fractions (FIG. 3). However, the islets which were derived from TNAP$^+$CD56$^+$ MSC were larger, and the staining intensity of these markers was markedly more pronounced compared to TNAP$^+$CD56$^-$-derived or unfractionated MSC. In the undifferentiated MSC or in the differentiated cells which were labeled with an isotype-matching control antibody, no staining was observed.

Single Cell Analysis of the TNAP$^+$CD56$^-$ Clone

The growth characteristics, the phenotype and the differentiation capability of single TNAP$^+$CD56$^+$ and TNAP$^+$CD56$^-$ cells was determined by sorting single cells in gelatin-coated 96-well culture plates and culturing them in a serum-free medium until macroscopically visible colonies (>20 cells) appeared. The cloning efficiency of the sorted TNAP$^+$CD56$^+$ and TNAP$^+$CD56$^+$ cells was 11/96 and 5/96 respectively. This ca. twofold increased frequency of the CD56$^+$ cells is consistent with the twofold increased colony values of the sorted cells described in FIG. 2D.

The resulting colonies were transferred into T-25 bottles and expanded until they reached 60 to 70% confluence. A phenotype analysis showed that all 16 clones were negative for CD45, but expressed CD73, CD90, CD105 and CD166, and they also exhibited reduced CD271 expression (FIG. 4A, FIG. 6: Table 2). All CD56$^+$ clones, except for the clone C3, downregulated CD56 expression. In contrast to this, CD56 expression was induced in two out of four MSC clones which were derived from CD56$^-$ cells (C14 and C15. Interestingly, significant CD34 expression could be observed in two of the CD56$^+$ and CD56$^-$ clones, whereas TNAP was detected only in one CD56$^+$ clone and in four out of five CD56$^-$ clones. Frizzled-9 expression was also only observed in four out of eleven CD56$^+$ clones, and in all CD56$^-$ clones. These data show that each single clone has an individual expression profile, with preferred expression of TNAP and frizzled-9 in the CD56$^-$ clones.

Expansion of all 16 single cells over 24 days led to the appearance of spindle-shaped cells with a fibroblast-like morphology (FIG. 4B). Among the single clones, a marked heterogeneity was observed as regards proliferation potential (FIG. 6: Table 2). Although the average number of the cells which were derived from CD56$^+$ clones was about twice as high as that of the cells derived from the CD56$^-$ clones (93.5× 10$^3$ compared to 52.8×10$^3$ after culturing for 24 days), no connection could be detected between the single clones or the phenotype profiles (FIG. 6: Table 2).

The strongly proliferating clones C1 and C2 (TNAP⁺CD56⁺) and C12 and C13 (TNAP⁺CD56⁻) were also analyzed as regards their osteoblastic, adipocytic and neuronal differentiation potential. From FIG. 4C it can be seen that only one CD56⁻ clone, but none of the CD56⁺ clones, led to the formation of Oil Red O dye-incorporating adipocytes. Alkaline phosphatase-positive osteoblasts and neuronal β-tubulin III-expressing neurone-like cells were generated from three out of four clones, but not by the CD56⁻ clone C13 (FIG. 4C). It was remarkable that β-tubulin III-positive cells were 5 to 10 times more common in the CD56⁺ clones than in the CD56⁻ clones.

Transfection of HEK-293 Cells With TNAP

HEK-293 cells (obtainable from the German Collection of Microorganisms and Cell Cultures, DSMZ, under the number DSMZ No. ACC 305) were transfected with the coding sequence of TNAP/ALPL (Homo sapiens alkaline phosphatase, liver/bone/kidney (ALPL)) which was integrated into the vector pCMV6-AC-GFP (obtainable from Origene Technologies, Rockville, Md., USA). For the transfection, the reagent MegaTran1.0 transcript 1 (also OriGene Technologies, Rockville, Md., USA) was used. After the incubation, the cells were washed and labeled with W8B2-APC. The flow cytometry analysis (see FIG. 7) shows that ca. 40% of the cells are strongly positive for W8B2: as well as TNAP (W8B2 antigen) (FIG. 7A), the cells also express the reporter gene green fluorescent protein (GFP) (FIG. 7B).

Detection of Alkaline Phosphatase Activity

Bone marrow cells were labeled with the TNAP-specific antibody W8B2 (W8B2-APC) and sorted in the FACSAria (BD Biosciences, Franklin Lakes, N.J. USA) cell sorter. The sorted cells were then stained with a commercially available kit for the detection of alkaline phosphatase (StemTAG AP staining kit; Stem Cell Technologies, Vancouver, CA). Only W8B2-positive cells showed a reaction for this enzyme (FIG. 8A). W8B2-negative cells showed no reaction (FIG. 8B).

With the present results, MSC populations which were recognized by CD56-specific and TNAP-specific antibodies were characterized. It was remarkable that effective chondrocyte and pancreas-like islet differentiation could only be induced in cases of the TNAP⁺CD56⁺ fraction. In contrast to this, adipocytes could only be generated from TNAP⁺CD56⁻ cells. Sorting out of individual cells from both subsets confirmed the different proliferation and differentiation capability of the TNAP⁺CD56⁺ and TNAP⁺CD56⁻ cells.

With the present results, it could also be shown that only the TNAP⁺CD56⁺ cells were capable of effectively differentiating into chondrocytes, as could be shown by the increased cartilage pellet size and the extensive proteoglycan staining.

Hence with the present study antigens were identified, namely TNAP and CD56, by means of which MSC with chondrogenic, adipocytic or pancreatic differentiation potential can be effectively identified and/or identified.

These results are particularly relevant with regard to the clinical use of the stem cells thus isolated or the chondrocytes/adipocytes/pancreas-like cells obtained via these stem cells. Thus for example injuries of the articular cartilage and disks are always difficult to treat, precisely because of the limited regeneration capability of these tissues. Diseases such as rheumatoid arthritis, traumata, bone fractures and disk injuries are directly associated with the lack of effective chondrogenesis. In spite of the progress in orthopedics and the growing success in autologous chondrocyte transplantation, cell biology-based approaches for cartilage regeneration remain a challenge. The main problem is the use of cultured cells, the starting cells for which are only poorly characterized, for clinical purposes.

Hence the present invention offers the possibility of providing highly enriched and well defined TNAP⁺CD56⁺ bone marrow cells with outstanding chondrogenic differentiation capability, which can be used for clinical application as starting culture or population. These cells can either be used directly for injection, for example into the intervertebral disk spaces/disks, or be expanded and differentiated into chondrocytes in vitro, before they are used for clinical applications.

What is claimed is:

1. A method for isolating and/or identifying of stem cells with adipocytic, chondrocytic and pancreatic differentiation potential, wherein the method comprises the step of contacting a sample containing stem cells with an antibody which binds to the antigen TNAP (tissue non-specific alkaline phosphatase) and isolating and/or identifying the stem cells to which the antibody binding the TNAP antigen has bound, and wherein in addition a second antibody or functional, antigen-binding fragments of the second antibody, is contacted with said sample, wherein the second antibody binds to CD56.

2. The method as claimed in claim 1, wherein the antibody which binds to the antigen TNAP is selected from the group consisting of:
   antibody W8B2 which is produced by the cell line deposited at the German Collection of Microorganisms and Cell Cultures with the No. ACC 2567,
   functional, antigen-binding fragments of the antibody W8B2 which is produced by the cell line deposited at the German Collection of Microorganisms and Cell Cultures with the No. ACC 2567, and
   an antibody which binds to the same epitope as the antibody W8B2 which is produced by the cell line deposited at the German Collection of Microorganisms and Cell Cultures with the No. ACC 2567.

3. The method as claimed in claim 1, wherein the antibody binding to CD56 is selected from the group of:
   the antibody 39D5 which is produced by the cell line deposited at the German Collection of Microorganisms and Cell Cultures with the No. ACC 2930,
   functional, antigen-binding fragments of the antibody 39D5 which is produced by the cell line deposited at the German Collection of Microorganisms and Cell Cultures with the No. ACC 2930,
   an antibody which binds to the same antigen as the antibody 39D5 which is produced by the cell line deposited at the German Collection of Microorganisms and Cell Cultures with the No. ACC 2930, and
   an antibody which binds to the same epitope as the antibody 39D5 which is produced by the cell line deposited at the German Collection of Microorganisms and Cell Cultures with the No. ACC 2930.

4. The method as claimed in claim 1, wherein in addition to the combination of an anti-TNAP and an antibody directed against CD56, an antibody directed against CD271, or functional, antigen-binding fragments of the anti-CD271 antibody, is used.

5. A method for the isolation and/or identification of mesenchymal stem cells with adipocytic differentiation potential, wherein the method comprises the following steps:
   a) contacting a sample which contains mesenchymal stem cells with an antibody which binds to the antigen TNAP (tissue non-specific alkaline phosphatase), or with functional, antigen-binding fragments of the antibody,
   b) contacting the sample from step a) with an antibody which binds to CD56, or with functional, antigen-binding fragments of the antibody, and
   c) isolation and/or identification of cells to which the antibody which binds to the antigen TNAP, or functional, antigen-binding fragments of the antibody, but not the antibody which binds to CD56, or functional, antigen-binding fragments of the antibody, has bound.

6. The method as claimed in claim 5, wherein the anti-TNAP antibody used in step a) is selected from the group consisting of:
- antibody W8B2 which is produced by the hybridoma cell line deposited at the German Collection of Microorganisms and Cell Cultures with the No. ACC 2567,
- functional, antigen-binding fragments of the antibody W8B2, and
- antibodies which bind to the same epitope as the antibody W8B2 which is produced by the hybridoma cell line deposited at the German Collection of Microorganisms and Cell Cultures with the No. ACC 2567.

7. The method as claimed in claim 5, wherein the antibody binding to CD56 used in step b) is selected from the group consisting of:
- antibody 39D5 which is produced by the hybridoma cell line deposited at the German Collection of Microorganisms and Cell Cultures with the No. ACC 2930,
- functional, antigen-binding fragments of the antibody 39D5, and
- antibodies which bind to the same epitope as the antibody 39D5 which is produced by the hybridoma cell line deposited at the German Collection of Microorganisms and Cell Cultures with the No. ACC 2930.

8. A method for the isolation and/or identification of mesenchymal stem cells with chondrocytic differentiation potential, wherein the method comprises the following steps:
a) contacting a sample which contains mesenchymal stem cells with an antibody which binds to the antigen TNAP, or with functional, antigen-binding fragments of the antibody,
b) contacting the sample from step a) with an antibody which binds to CD56, or with functional, antigen-binding fragments of the antibody, and
c) isolation and/or identification of cells to which both the antibody which binds to the antigen TNAP, or functional, antigen-binding fragments of the antibody, and also the antibody which binds to CD56, or functional, antigen-binding fragments of the antibody, have bound.

9. The method as claimed in claim 8, comprising a further step c'):
c') contacting the sample from step b) with an antibody which binds to CD271, or with functional, antigen-binding fragments of the antibody.

10. The method as claimed in claim 8, wherein the anti-TNAP antibody used in step a) is selected from the group consisting of:
- antibody W8B2 which is produced by the hybridoma cell line deposited at the German Collection of Microorganisms and Cell Cultures with the No. ACC 2567,
- functional, antigen-binding fragments of the antibody W8B2, and
- antibodies which bind to the same epitope as the antibody W8B2 which is produced by the hybridoma cell line deposited at the German Collection of Microorganisms and Cell Cultures with the No. ACC 2567.

11. The method as claimed in claim 9, wherein the antibody binding to CD56 used in step b) is selected from the group consisting of:
- antibody 39D5 which is produced by the hybridoma cell line deposited at the German Collection of Microorganisms and Cell Cultures with the No. ACC 2930,
- functional, antigen-binding fragments of the antibody 39D5, and
- antibodies which bind to the same epitope as the antibody 39D5 which is produced by the hybridoma cell line deposited at the German Collection of Microorganisms and Cell Cultures with the No. ACC 2930.

* * * * *

UNITED STATES PATENT AND TRADEMARK OFFICE
CERTIFICATE OF CORRECTION

PATENT NO. : 9,052,316 B2
APPLICATION NO. : 12/980092
DATED : June 9, 2015
INVENTOR(S) : Hans-Joerg Buehring et al.

It is certified that error appears in the above-identified patent and that said Letters Patent is hereby corrected as shown below:

IN THE CLAIMS

Column 18 line 24, "claim 9" should be changed to --claim 8--.

Signed and Sealed this
Sixth Day of October, 2015

Michelle K. Lee
*Director of the United States Patent and Trademark Office*